US011382495B2

(12) United States Patent
Awadu

(10) Patent No.: US 11,382,495 B2
(45) Date of Patent: Jul. 12, 2022

(54) ENDOSCOPE HANGER, ENDOSCOPE HOLDING METHOD, AND CART, CLEANING SINK, CLEANING AND DISINFECTING DEVICE, STAND, AND ENDOSCOPE STORAGE CABINET HAVING SAID ENDOSCOPE HANGER

(71) Applicant: Satoshi Awadu, Nagasaki (JP)

(72) Inventor: Satoshi Awadu, Nagasaki (JP)

( * ) Notice: Subject to any disclaimer, the term of this patent is extended or adjusted under 35 U.S.C. 154(b) by 236 days.

(21) Appl. No.: 15/555,274

(22) PCT Filed: Mar. 2, 2016

(86) PCT No.: PCT/JP2016/056513
§ 371 (c)(1),
(2) Date: Sep. 1, 2017

(87) PCT Pub. No.: WO2016/140290
PCT Pub. Date: Sep. 9, 2016

(65) Prior Publication Data
US 2018/0049834 A1    Feb. 22, 2018

(30) Foreign Application Priority Data

Mar. 2, 2015    (JP) .............................. JP2015-040817

(51) Int. Cl.
*A61B 1/00*  (2006.01)
*G02B 23/24*  (2006.01)
(Continued)

(52) U.S. Cl.
CPC ........ *A61B 1/00147* (2013.01); *A61B 1/0014* (2013.01); *A61B 1/00128* (2013.01);
(Continued)

(58) Field of Classification Search
CPC ......... A61B 50/22; A61B 50/24; A61B 50/26; A61B 50/28; A61B 50/00; A61B 50/10;
(Continued)

(56) References Cited

U.S. PATENT DOCUMENTS

| 4,854,301 A   | 8/1989 | Nakajima |
| 5,415,287 A * | 5/1995 | Hamano ................ A61B 50/24 |
|               |        | 383/33 |

(Continued)

FOREIGN PATENT DOCUMENTS

| JP | S55 85003 U   | 6/1980 |
| JP | S63-122416 A  | 5/1988 |

(Continued)

OTHER PUBLICATIONS

Office Action for corresponding European Application No. 16758983.7 dated Feb. 3, 2020.

*Primary Examiner* — Ryan N Henderson
(74) *Attorney, Agent, or Firm* — Renner, Otto, Boisselle & Sklar, LLP

(57) ABSTRACT

An endoscope hanger which frees a doctor's hands without causing pain to a patient, and a cart, washing sink, washing and sterilization apparatus, stand, and endoscope storage cabinet having said endoscope hanger are provided. This endoscope hanger is characterized by having a polygonal shape and/or an ellipsoid shape (including a perfect circular shape) or a shape that is a combination of these, and is characterized by having at least one hole that can hold an endoscope at an oblique angle; this cart, washing sink, washing and sterilization apparatus, stand, and endoscope storage cabinet comprise said endoscope hanger.

20 Claims, 11 Drawing Sheets

(51) Int. Cl.
*A61B 50/24* (2016.01)
*A61B 90/57* (2016.01)
*A61B 50/20* (2016.01)
*A61B 50/13* (2016.01)
*A61B 50/22* (2016.01)
*A61B 90/50* (2016.01)
*A61B 50/10* (2016.01)
*A61B 1/12* (2006.01)

(52) U.S. Cl.
CPC .......... *A61B 1/00142* (2013.01); *A61B 50/13* (2016.02); *A61B 50/20* (2016.02); *A61B 50/22* (2016.02); *A61B 50/24* (2016.02); *A61B 90/50* (2016.02); *A61B 90/57* (2016.02); *G02B 23/24* (2013.01); *A61B 1/121* (2013.01); *A61B 2050/105* (2016.02)

(58) Field of Classification Search
CPC ... A61B 50/13; A61B 50/15; A61B 2050/105; A61B 2050/155; A61B 1/00112; A61B 1/00114; A61B 1/00117; A61B 1/00119; A61B 1/00121; A61B 1/00124; A61B 1/00126; A61B 1/00128; A61B 1/00131; A61B 1/0014; A61B 1/00147
See application file for complete search history.

(56) References Cited

U.S. PATENT DOCUMENTS

| | | | | |
|---|---|---|---|---|
| 6,126,591 A * | 10/2000 | McGarry | ........... | G02B 23/2476 600/101 |
| 6,549,333 B1 * | 4/2003 | Nakatate | ........... | A61B 90/20 359/368 |
| 6,716,159 B2 * | 4/2004 | Takase | ........... | A61B 1/00142 600/102 |
| D671,213 S * | 11/2012 | Funakoshi | ........... | D24/138 |
| D671,214 S * | 11/2012 | Funakoshi | ........... | D24/138 |
| 8,821,379 B2 * | 9/2014 | Motoki | ........... | A61B 1/0005 600/137 |
| D723,684 S * | 3/2015 | Funakoshi | ........... | D24/138 |
| 9,522,043 B1 * | 12/2016 | Hoftman | ........... | A61B 50/28 |
| 10,383,509 B2 * | 8/2019 | Greenburg | ........... | A61B 90/50 |
| 2002/0123663 A1 * | 9/2002 | Takase | ........... | A61B 1/00142 600/102 |
| 2005/0234297 A1 * | 10/2005 | Devierre | ........... | A61B 1/00087 600/129 |
| 2006/0106280 A1 * | 5/2006 | Surti | ........... | A61B 90/53 600/102 |
| 2006/0253109 A1 * | 11/2006 | Chu | ........... | A61B 90/50 606/1 |
| 2008/0033454 A1 * | 2/2008 | Lukoschek | ........... | A61B 90/50 600/417 |
| 2008/0208002 A1 * | 8/2008 | Maruyama | ........... | A61B 1/0052 600/131 |
| 2008/0314789 A1 * | 12/2008 | Thomas | ........... | A61L 2/26 206/572 |
| 2010/0191049 A1 * | 7/2010 | Mandava | ........... | A61B 1/00144 343/702 |
| 2010/0286478 A1 * | 11/2010 | Ewers | ........... | A61B 1/00133 600/114 |
| 2011/0066979 A1 * | 3/2011 | Matsui | ........... | A61B 1/04 715/823 |
| 2011/0083983 A1 * | 4/2011 | Walters | ........... | A61B 50/20 206/370 |
| 2011/0172490 A1 * | 7/2011 | Ishikawa | ........... | G02B 23/2476 600/102 |
| 2012/0118088 A1 * | 5/2012 | Smith | ........... | A61B 1/00154 384/15 |
| 2012/0172850 A1 * | 7/2012 | Kappel | ........... | A61B 1/00149 606/1 |
| 2012/0187104 A1 * | 7/2012 | Heymann | ........... | A61B 50/20 219/385 |
| 2012/0197075 A1 * | 8/2012 | Krimsky | ........... | A61B 1/00149 600/102 |
| 2012/0213572 A1 * | 8/2012 | Mischnick | ........... | A61B 90/50 403/5 |
| 2013/0001180 A1 * | 1/2013 | Stout | ........... | A61B 50/20 211/85.13 |
| 2013/0079594 A1 * | 3/2013 | Motoki | ........... | G02B 23/2484 600/109 |
| 2013/0327663 A1 * | 12/2013 | Telford | ........... | A61B 46/23 206/363 |
| 2014/0021079 A1 * | 1/2014 | Koller | ........... | A61B 50/00 206/370 |
| 2014/0116647 A1 * | 5/2014 | Kannry | ........... | A61B 50/13 165/80.5 |
| 2014/0163318 A1 * | 6/2014 | Swanstrom | ........... | A61B 17/34 606/49 |
| 2014/0163327 A1 * | 6/2014 | Swanstrom | .... | A61B 17/320016 600/235 |
| 2014/0223701 A1 * | 8/2014 | Bean | ........... | A61B 1/00066 24/483 |
| 2015/0057537 A1 * | 2/2015 | Dillon | ........... | A61B 1/0014 600/113 |
| 2015/0320392 A1 * | 11/2015 | Missov | ........... | A61B 8/4455 600/462 |
| 2016/0074628 A1 * | 3/2016 | Smith | ........... | H04N 5/2253 604/174 |
| 2016/0331452 A1 * | 11/2016 | Oguni | ........... | A61B 1/018 |
| 2017/0143188 A1 * | 5/2017 | Oskin | ........... | A61B 1/00128 |
| 2017/0265723 A1 * | 9/2017 | Yamaya | ........... | A61B 1/018 |
| 2019/0175296 A1 * | 6/2019 | Tate | ........... | A61B 90/98 |

FOREIGN PATENT DOCUMENTS

| | | | |
|---|---|---|---|
| JP | S64-22302 | | 2/1989 |
| JP | 11113835 A | * | 4/1999 |
| JP | 11151199 A | * | 6/1999 |
| JP | 11290262 A | * | 10/1999 |
| JP | 2000316792 A | * | 11/2000 |
| JP | 2001-212069 A | | 8/2001 |
| JP | 2002224013 A | * | 8/2002 |
| JP | 2003250750 A | * | 9/2003 |
| JP | 2004081635 A | * | 3/2004 |
| JP | 2006-25883 A | | 2/2006 |
| JP | 2009-183358 A | | 8/2009 |
| WO | WO 2012/084264 A1 | | 6/2012 |

* cited by examiner

[plan view]

[A-A line cross-sectional view]

[B-B line cross-sectional view]

[bottom view]

ENDOSCOPE HANGER, ENDOSCOPE HOLDING METHOD, AND CART, CLEANING SINK, CLEANING AND DISINFECTING DEVICE, STAND, AND ENDOSCOPE STORAGE CABINET HAVING SAID ENDOSCOPE HANGER

TECHNICAL FIELD

The present invention relates to a scope hanger for holding an endoscope, a method for holding an endoscope, a cart having the same, a washing sink, a washing and sterilizing apparatus, a stand and a storage cabinet for an endoscope.

BACKGROUND ART

When using an endoscope (scope) for examination or treatment, if there is an endoscope holding stand capable of holding the endoscope, the hand of a doctor becomes free, and convenience can be expected such as being able to prevent the doctor's exposure to radiation when using radiation for examination or treatment, being able to do quick treatment at the time of emergency, being able to adjust the instruments used for examination or treatment, being able to rest a weary doctor by long-term treatment it can. As an invention of such an endoscope holding stand, Patent Literature 1 and the like are available. However, as compared with the case that a doctor holds it, there are problems to cause pain to a patient, because the endoscope is rotated counterclockwise by 120 degrees when viewed from above and held vertically from side view, that it is necessary to release the endoscope to be held by the assistant and to operate it with both hands of the doctor and that holding height is not constant depending on the physique difference of the assistants when a doctor releases the endoscope to be held by an assistant.

Therefore, development of a holding member capable of holding an endoscope without causing pain to a patient and a cart and the like having the holding member have been desired.

RELATED ART DOCUMENTS

Patent Documents

Patent literature 1: Japanese Laid-Open Patent Publication No. 2009-183358

SUMMARY OF THE INVENTION

An endoscope hanger which frees a doctor's hands without causing pain to a patient, and a cart, washing sink, washing and sterilizing apparatus, stand and endoscope storage cabinet having said endoscope hanger are provided. This endoscope hanger is characterized by having a polygonal shape and/or an ellipsoid shape (including a perfect circular shape) or a shape that is a combination of these, and is characterized by having at least one hole that can hold an endoscope at an oblique angle; this cart, washing sink, washing and sterilizing apparatus, stand and endoscope storage cabinet comprise said endoscope hanger.

Problem to be Solved by the Invention

An endoscope holding member (scope hanger) that a doctor can use hand freely without causing pain to a patient and a cart having it, a washing sink, a washing and sterilizing apparatus, a stand and a storage cabinet for an endoscope.

Means for Solving the Problem (1) An endoscope holding member (a scope hanger), characterized by having at least one hole which has a polygonal shape and/or an elliptical shape (including perfect circle) or a mixed shape thereof and which can hold the endoscope at an oblique angle.

(2) The endoscope holding member according to (1), having polygonal and/or elliptical (including perfect circle) or mixed shapes thereof, having at least two holes capable of holding an endoscope, wherein the first hole can hold the endoscope vertically, wherein the second hole can hold the endoscope at an oblique angle.

(3) The endoscope holding member according to (1) or (2), characterized by having polygonal and/or elliptical (including perfect circle) or mixed shapes thereof, and by having a thickness of 1 cm to 5 cm, a length of 8 cm to 15 cm, a width of 20 cm to 30 cm, a thickness of 1 cm to 5 cm, a major axis of 20 cm to 30 cm, a minor diameter of 8 cm to 15 cm.

(4) The endoscope holding member according to any one of (1) to (3) wherein said oblique angle is 20 to 80 degrees.

(5) The endoscope holding member according to any one of (1) to (4) wherein the number of holes capable to hold said endoscopes is 4 to 24.

(6) The endoscope holding member according to any one of (1) to (5) characterized in that it can respond to changes in the insertion length of the endoscope and the position of the patient by merely rotating the endoscope holding member at the height of the upper end of the support portion which is set to the height held by the doctor in advance.

(7) The endoscope holding member according to any one of (1) to (5), characterized by being capable to hold multiple different kinds of endoscopes.

(8) A cart comprising, an endoscope holding member according to any one of (1) to (7), a support portion supporting the holding member so as to be rotatable in a horizontal direction and vertically movably supporting the holding member, and means for securing the support portion.

(9) A cart according to (8), comprising two or more support portion described in (1) to (7).

(10) A cart according to (8) or (9), comprising said support portion at the front right corner.

(11) A method for holding an endoscope using the cart according to (8) to (10).

(12) A washing sink, a washing and sterilizing apparatus, a stand or an endoscope storage cabinet, comprising the holding member described in any one of (1) to (7).

(13) A washing sink, a washing and sterilizing apparatus, a stand or an endoscope storage cabinet according to (12) wherein said holding member is supported rotatable.

(14) A method for holding an endoscope using a washing sink, a washing and sterilizing apparatus, a stand or an endoscope storage cabinet described in (12) or (13).

(15) A method according to (14), wherein said endoscopes are multiple different kinds of endoscopes.

(16) A method for holding an endoscope stably using the endoscope holding member according to (1) to (7).

(17) A method according to (16), characterized in that a hardness adjusting ring is passed vertically through a hole on a back side of the endoscope holding member and then the endoscope is moved and held in a hole in front of the endoscope holding member,

(18) A method according to (16) or (17), characterized in that the endoscope is supported by three points, comprising one point under the endoscope and two points of upper side surface in case of holding at an oblique angle.

Effects of the Invention

According to the present invention, the flexibility of the doctor is raised drastically without causing pain to a patient when using an endoscope.

DESCRIPTION OF THE EMBODIMENTS

Figure 1:
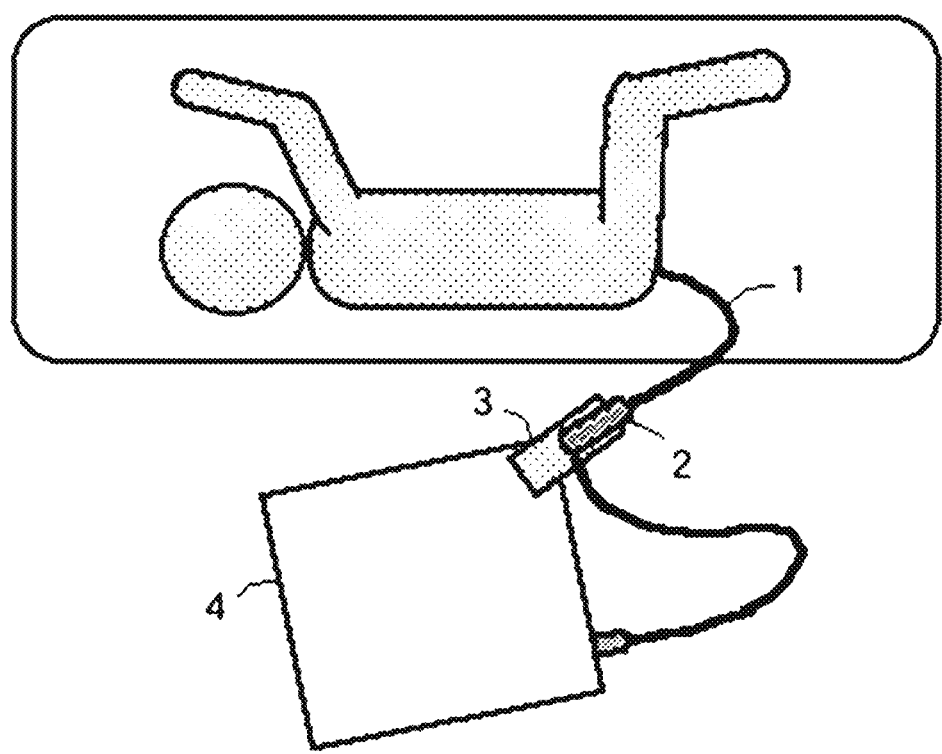
FIG. 1 is a plan view showing a state in which a scope hanger holds an endoscope operation part at an oblique angle with the same height as the doctor holds the colonoscope while being inserted in the patient.

The present invention comprise a mean that can hold an endoscope at a specific angle and a holding means to hold the holding means rotatable. As a mean for fixing and holding at a specific angle, holding members having the shape of a rectangular parallelepiped or a similar polygon or elliptical shape, or a combination thereof can be used. As a means for fixing and holding the endoscope at a specific angle, it may be a structure like a clamp, but it is necessary to fix it so that the angle does not change during holding.

In the present invention, the term "endoscope" means a medical device aimed at observing the interior of a living body, and has an optical system incorporated in the main body, and watching the image inside the living body by inserting the tip into the living body. Examples of the endoscope include a gastroscope, a colonoscope, an enteroscope, a cholangiopancreatoscope, a laryngoscope, a bronchoscope, a cystoscope, an ureteroscope, a hysteroscope, an arthroscope, a neruoendoscope, and the like, but not limited thereto.

The material of said holding member is not particularly limited as long as it can stably hold the endoscope such as wood, plywood, plastic, metal, rubber, etc.

When there is a hole in the endoscope holding member, it has at least two types of holes that can hold both in the vertical direction and the oblique angle. If necessary, these two holes may be connected. By connecting the two holes, the area of the endoscope holding member can be reduced.

In addition, by connecting the two holes, making the hole on the back side (center side) large enough to pass the hardness adjusting ring vertically and the hole on the front side (end side) as the hole capable of holding the endoscope, after the hardness adjusting ring is passed through the hole on the back side, the endoscope can be stably held by moving it to the hole on the front side. In this case, the diameter of the hole on the back side (center side) is preferably larger than the diameter of the hardness adjusting ring by 2.0 mm to 3.0 mm. More preferably, the diameter is larger by 2.1 mm to 2.7 mm, further preferably by 2.2 mm to 2.4 mm. Further, the length of the boundary part between the hole on the back side (center side) and the hole on the front side (end side) is preferably larger than the diameter of the endoscope operation part of the Olympus by 2.0 mm to 2.5 mm. More preferably, it is larger by 2.1 mm to 2.4 mm, further preferably by 2.2 mm to 2.3 mm.

In the case of wood, the hole of the endoscope holding member may be scraped to optimize the angle. In the case of rubber or plastics, it may be integrally molded with a metal mold or the like, and metal or the like may be manufactured by a manufacturing method well known by those skilled in the art such as press working. In the case of plastic or the like, it may be manufactured using a three-dimensional printer.

A preferable angle when holding the endoscope is a vertical direction when the endoscope is not used. In this case, it may not be completely vertical, and an angle of ±5 degrees in the vertical direction is preferable. A more preferable angle is ±3 degrees in the vertical direction, further preferably ±1 degree in the vertical direction.

When holding the endoscope obliquely during examination or treatment, the oblique angle is preferably 20 to 80 degrees with respect to the horizontal direction. This angle is the same as the angle at which the doctor holds the endoscope by hand.

In the case of a colonoscope, the oblique angle is preferably 40 to 50 degrees, more preferably 41 to 48 degrees, further preferably 42 to 46 degrees, and most preferably 43 to 45 degrees with respect to the horizontal direction.

In the case of a gastroscope, the oblique angle is preferably 40 to 50 degrees, more preferably 42 to 48 degrees, most preferably 43 to 47 degrees with respect to the horizontal direction.

In the case of a bronchoscope, the oblique angle is preferably 25 to 35 degrees, more preferably 27 to 33 degrees, most preferably 28 to 32 degrees with respect to the horizontal direction.

In the case of an ureteroscope, the oblique angle is preferably 65 to 75 degrees, more preferably 67 to 73 degrees, most preferably 68 to 72 degrees with respect to the horizontal direction.

When the endoscope holding member is attached to a cart, preferably, the endoscope holding member is rotatably supported by the support post. Rotation is horizontal, but it may be within horizontal ±5 degrees even if it is not perfectly horizontal. By making it rotatable, it is possible to adjust so that the endoscope can be easily held. That is, when the longer part is inserted, the holding member is rotated so as to be closer, and when the short part is inserted, by rotating the holding member to be farther away, it is possible to easily hold the surplus endoscope without giving a burden.

In order to delay the falling of the scope hanger, it is also possible to use an infusion pole (for example, manufactured by AS ONE Corporation) with an air damper on the outer cylinder part and/or the inner cylinder part of the scope hanger. In this case, it is preferable to enlarge the air hole at the lower end of the pole to weaken the effect of the air damper. After weaken the air damper effect, by drilling a hole at the lower end of the pole with the air damper, then a rubber cap is attached to the lower end of the pole to return the air damper effect to the original, furthermore, a small hole may be opened in the rubber cap so that the scope hanger apical end part (endoscope holding member) may have a damper effect such that it naturally lowers slowly. As a result, when the screw is loosened, it naturally lowers slowly, so there is no need to lower with the left hand, and there is no concern of collision due to rapid fall.

In a preferred embodiment, the post supporting the endoscope holding member is attached to the cart. More preferably, the right end of the front face of the cart (the left side facing the front of the cart) is preferable.

The endoscope holding member may be detachable and may be designed to be removable from the pole and sterilized.

Figure 16:
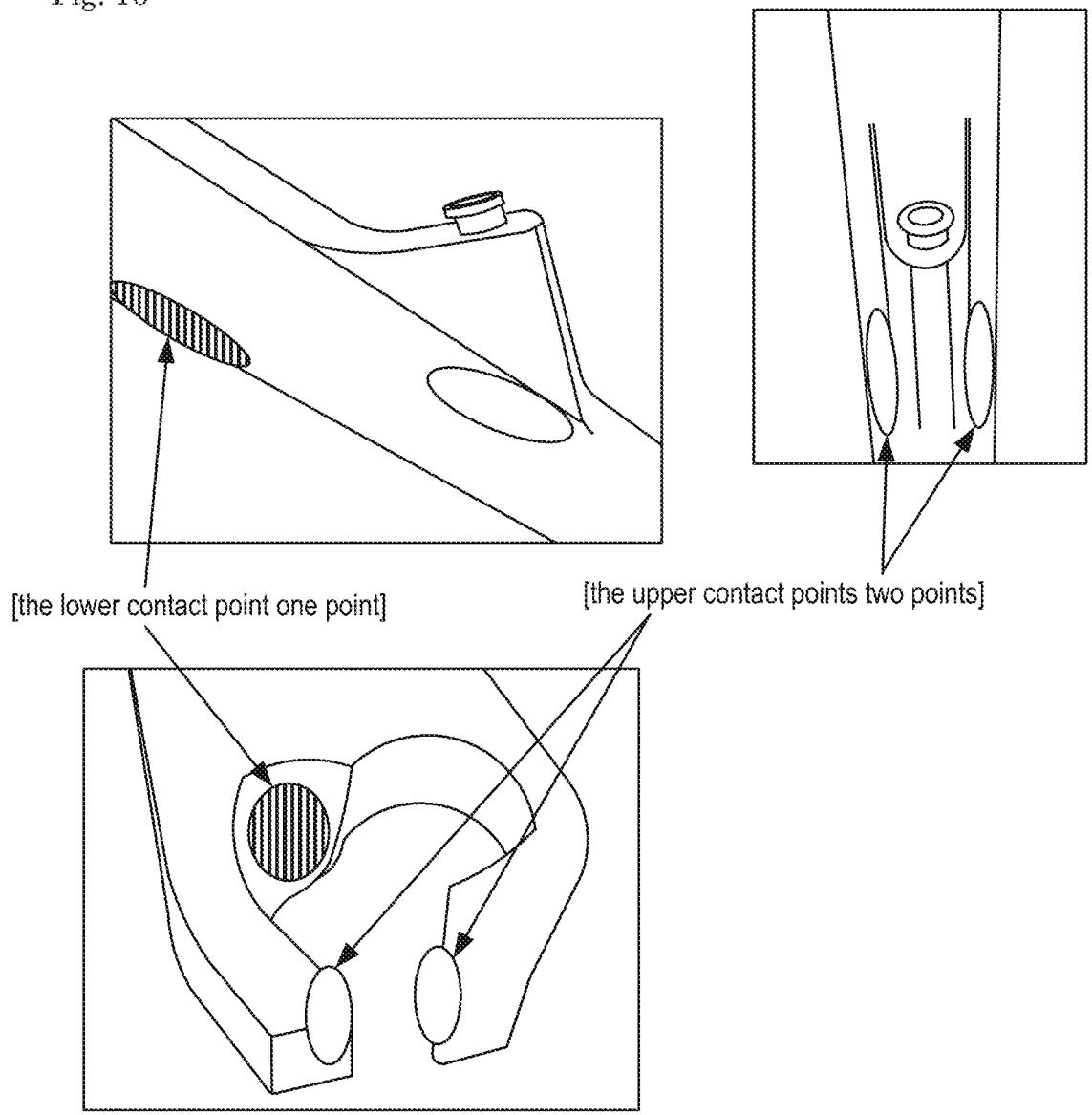
FIG. 16 is a figure showing contact part between the endoscope and the endoscope holding member of the present invention.

When holding the endoscope, it can usually be held with the center of the endoscope operation part. In addition, when holding an Olympus colonoscope, it may be held with the hardness adjusting ring or may be held with the center of the endoscope operation part, but preferably, when holding the Olympus colonoscope at an oblique angle, it is preferable to hold it with the hardness adjusting ring and when holding it in vertical direction, it is preferable to hold it with the center of the endoscope operation part. In the case of holding the endoscope obliquely, the endoscope can be stably held by being supported by the endoscope holding member, with at least a total of three points of one point on the lower surface of the endoscope and two points on the upper surface (FIG. 16). In the lower left drawing of FIG. 16, a circle part (lower contact point) of the border pattern (hatched part) above the hole on the end side of the endoscope holding member and the lower surface of the endoscope are in contact with each other, (Upper contact point) of the left and right white ellipse part and the upper surface of the endoscope come into contact and are supported. In this case, it is preferable to hold the endoscope with the forceps opening facing upward, but it is not limited thereto.

According to another aspect of the present invention, a cart, a washing sink, a washing and sterilization apparatus, a stand, and an endoscope storage cabinet are provided which are attached with a member that holds the endoscope whose holding angle is optimized and that is vertically and rotatably attached. The endoscope holding member is rotatably attached, and washing and sterilization and storage become more convenient. However, in the washing sink, the washing and sterilization apparatus, the stand and the endoscope storage cabinet, means for rotating is not indispensable. In the washing sink, the washing and sterilization apparatus, the stand and the endoscope storage cabinet, means for moving up and down are also not indispensable. Furthermore, not all of the endoscope holding member may be attached, but only a part thereof may be attached.

By using the holding member, the cart, the washing sink, the washing and sterilization apparatus, the stand or the endoscope storage cabinet having such a structure, it is possible to solve the problem at the time of holding the endoscope conventionally and the convenience at the time of examination, treatment, washing, sterilization, storage and taking out remarkably improved.

In addition, according to the present invention, six kind of shapes of the endoscope of at least three manufacturers can be held vertically by a endoscope holding member in a stable manner.

In the present specification, "being able to be held stably" means that it can be held without shake and in a state not to fall.

In the conventional storage cabinet, the place to store was determined for each shape of the endoscope, so it was managed by attaching tags. However, by using the endoscope holding member of the present invention, endoscopes having different shapes can be stored side by side in the same storage cabinet in order of sterilization, so that it can be known at a glance whether or not the endoscope has been sterilized, and there is an effect that it is possible to prevent a medical accident to use an unsterilized endoscope by mistake.

In addition, by using the endoscope holding member of the present invention for the stand temporarily holding the sterilized endoscope, even if the shape of the endoscope is different, the endoscope that has been sterilized is placed in the same place, so that it can be known at a glance whether or not it has been sterilized and there is an effect that it is possible to prevent a medical accident to use an unsterilized endoscope by mistake.

When holding the Olympus colonoscope vertically or at an oblique angle, it is more stable to hold with the center of the endoscope operation part than to hold with the hardness adjusting ring. In order to hold the Olympus colonoscope with the center of the endoscope operation part, the hardness adjusting ring must be passed vertically. However, if the hardness adjusting ring can be passed vertically through the part that holds the endoscope, the size of the part that holds the endoscope becomes large, and the endoscope can not be held stably. Therefore, if the size of the part is increased through which the forceps opening passes up and down and the hardness adjusting ring is allowed to pass up and down, when holding the Olympus colonoscope, hardness adjusting ring is passed from upper to lower at the part passing the forceps opening vertically, and the lower end of the endoscope operation part is moved from the part passing the forceps opening vertically to the part for holding the endoscope so that the endoscope is held vertically or at an oblique angle with the center of the endoscope operation part.

Further, it is also possible to enlarge the hole on the front side (end side) of the endoscope holding member, pass the hardness adjusting ring vertically and hold the endoscope by the hole on the back side (center side). In this case, since the forceps opening is held toward the center side, it is preferable to provide another hole for the forceps opening (total of 3 holes on one side). In this case, it may be difficult to hold at an oblique angle.

In addition, if the scope hanger apical end part can be integrated into one shape, there is no need to rotate the apical end part, so that a structure for rotation becomes unnecessary.

In order to make the scope hanger apical end part into one shape, it is necessary to make the part that holds the endoscope into one shape that can stably hold the center of the endoscope operation part of six kinds of shapes. In addition, in order to make the scope hanger apical end part into one shape, it is necessary to adjust the size of the part through which the forceps opening is passed up and down so that the hardness adjusting ring can pass through vertically. If the hardness adjusting ring can be passed up and down, the Olympus colonoscope can be held.

By setting the hole on the back side (center side) to a size that allows the hardness adjusting ring to pass up and down and making the hole on the front side (end side) to a shape capable of holding the six types of endoscopes, the scope hanger apical end part can be integrated into one shape. In this case, the diameter of the hole on the back side (center side) is preferably larger than the diameter of the hardness adjusting ring by 2.0 mm to 2.5 mm. More preferably, the diameter is larger by 2.1 mm to 2.4 mm, further preferably by 2.2 mm to 2.3 mm. In addition, the length of the boundary part between the hole on the back side (center side) and the hole on the front side (end side) is preferably larger than the diameter of the endoscope operation part of the Olympus colonoscope by 1.0 mm to 1.8 mm. It is more preferably larger by 1.1 mm to 1.6 mm, further preferably by 1.2 mm to 1.4 mm. Specific examples will be described below with reference to the drawings, but the present invention is not limited by these examples at all.

EXAMPLES

FIG. 1 shows a plan view of a state in which the scope hanger holds the endoscope operation part at an oblique angle with the same height as the doctor holds the colonoscope while being inserted in the patient.

Figure 2:
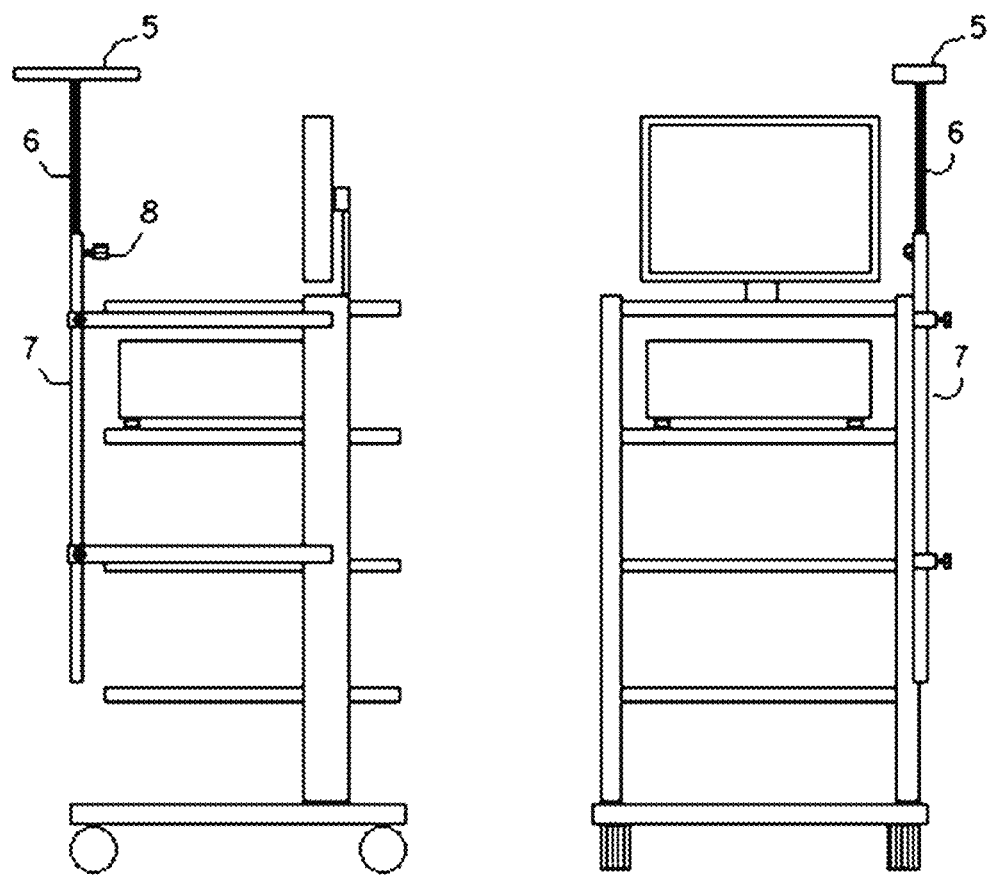
FIG. 2 is a figure of front view and side view showing the structure of the cart and the scope hanger.

In addition, FIG. 2 shows a front view and a side view of a cart on which a scope hanger is equipped.

When the endoscope operation part 2 is held by the scope hanger 3 at an oblique angle with the colonoscope 1 inserted in the patient, in order to hold the endoscope operation part 2 at the position closest to the position the doctor holds (or to hold the endoscope operation part 2 at the position closest to the patient), the scope hanger 3 is set up at the right corner of the front face of the cart 4.

If the endoscope is held at the same height and the same angle as the doctor holds it (that is, at an oblique angle), the excessive force is not applied to the patient or the endoscope. When the endoscope operation part 2 is held by the scope hanger 3 while the colonoscope 1 is inserted in the patient, it is necessary to make the shape of the scope hanger apical end part 5 such that the endoscope operation part 2 can be held at an oblique angle.

In addition, while waiting (when the endoscope is not inserted in the patient), since it is necessary to hold the endoscope operation part 2 vertically, it is necessary to make the shape of the scope hanger apical end part 5 to be able to hold the endoscope operation part 2 vertically.

Figure 3:
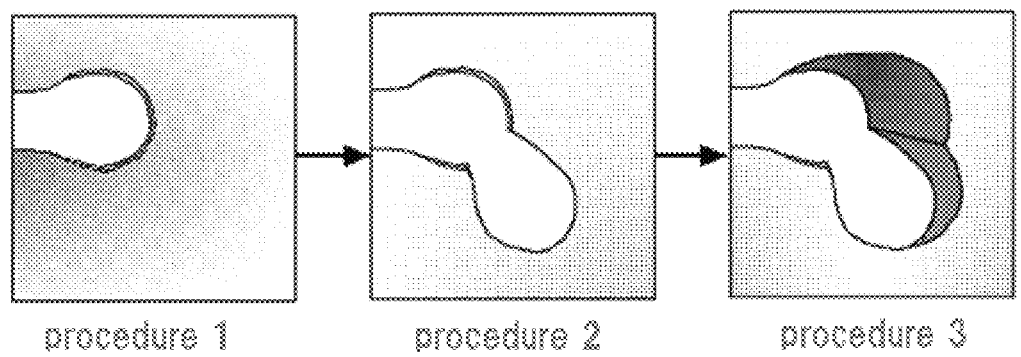
FIG. 3 is a plan view showing a method to determine a form of the scope hanger apical end part.

FIG. 3 shows a plan view of a method for determining the shape of the scope hanger apical end part.

The endoscope operation part 2 of the colonoscope 1 shows various shapes depending on the model. Therefore, in order to cope with the shape of the endoscope operation part 2 of all the colonoscope 1, six models of the colonoscope 1 of each manufacturer (Olympus, Fuji Film, and Pentax) were obtained.

Next, the wood of 2 cm in thickness, 10 cm in length, and 9 cm in width was shaved off, and the shape of the scope hanger apical end part 5 was determined for each type of colonoscope by the following procedure.

(1) First, the endoscope operation part 2 was shaped so as to be held vertically (FIG. 3, procedure 1).
(2) In addition, when holding the endoscope operation part 2 vertically, the forceps opening part (the projection at the lower end of the endoscope operation part) has to be passed vertically through the scope hanger apical end part 5, depending on the model, such a shape was added (FIG. 3, procedure 2).
(3) Furthermore, a shape that allows the endoscope operation part 2 to be held at an oblique angle is added (FIG. 3, procedure 3).

Among the six kinds of shapes of the scope hanger apical end part 5 determined as described above, those having similar shapes were examined while holding the endoscope operation part 2 of the colonoscope 1 of each manufacturer to integrate them into two kinds.

Figure 4:
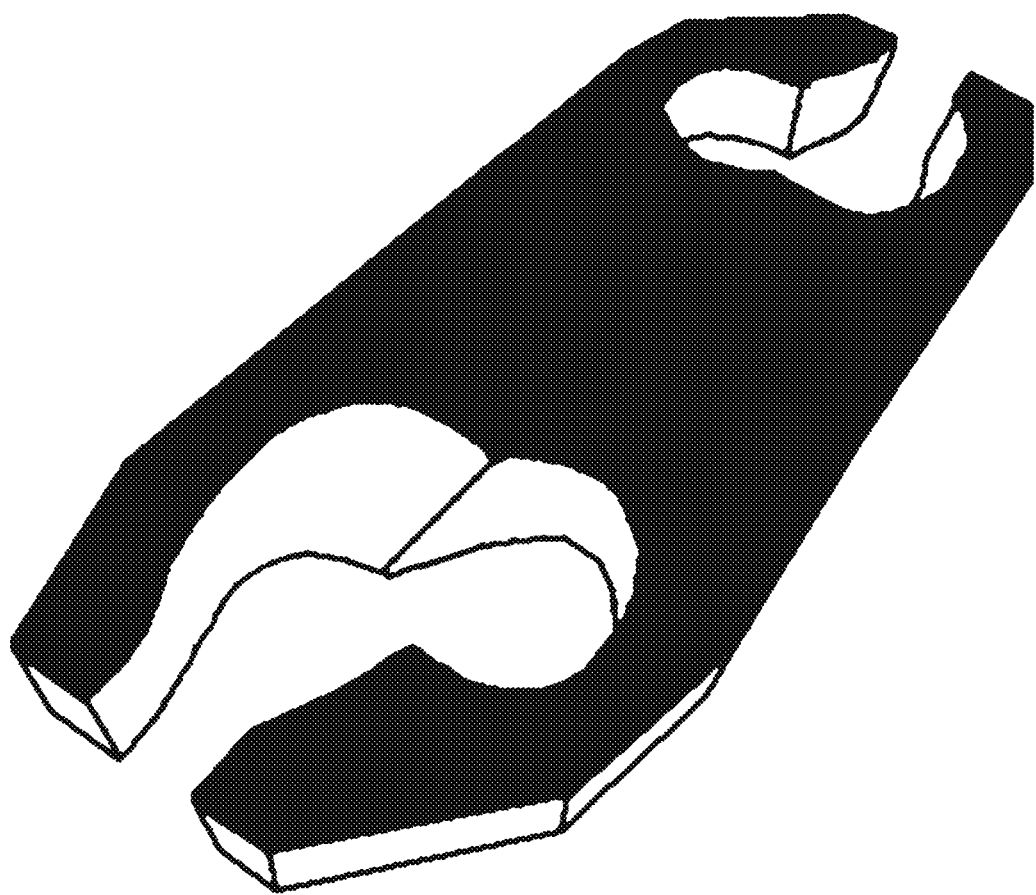
FIG. 4 is an oblique perspective figure showing the structure of the scope hanger apical end part.
Figure 5:
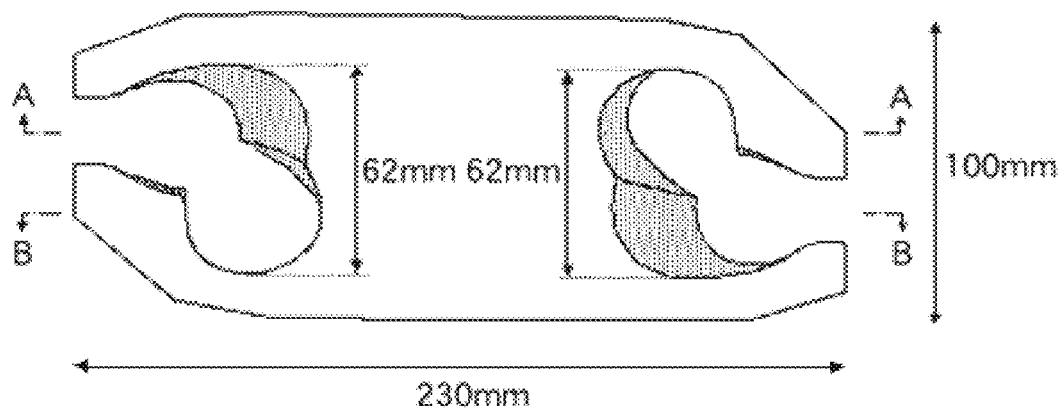
FIG. 5 is a plan view, cross-section view and bottom view showing the structure of the scope hanger apical end part.
Figure 5:
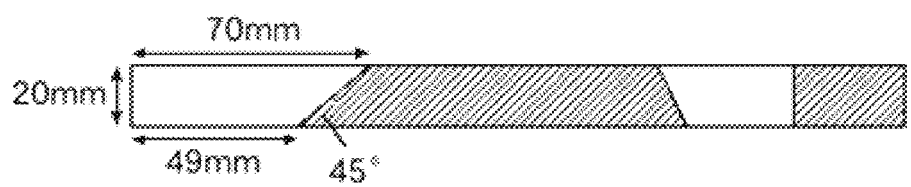
Figure 5:
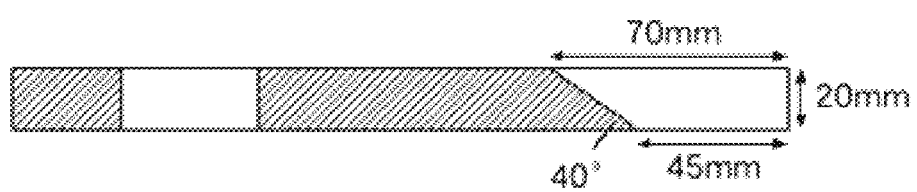
Figure 5:
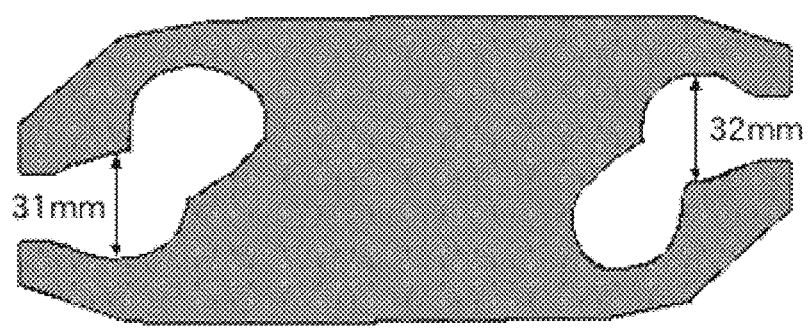

FIG. 4 shows a perspective view of the scope hanger apical end part, and FIG. 5 shows a plan view, a sectional view and a bottom view of the scope hanger apical end part.

The endoscope operation part 2 of each manufacturer's colonoscope 1 could be held at an oblique angle or vertically either on one of the scope hanger apical end parts 5 (49 mm×31 mm in the bottom view) or another one (45 mm×32 mm in the bottom view).

Figure 6:
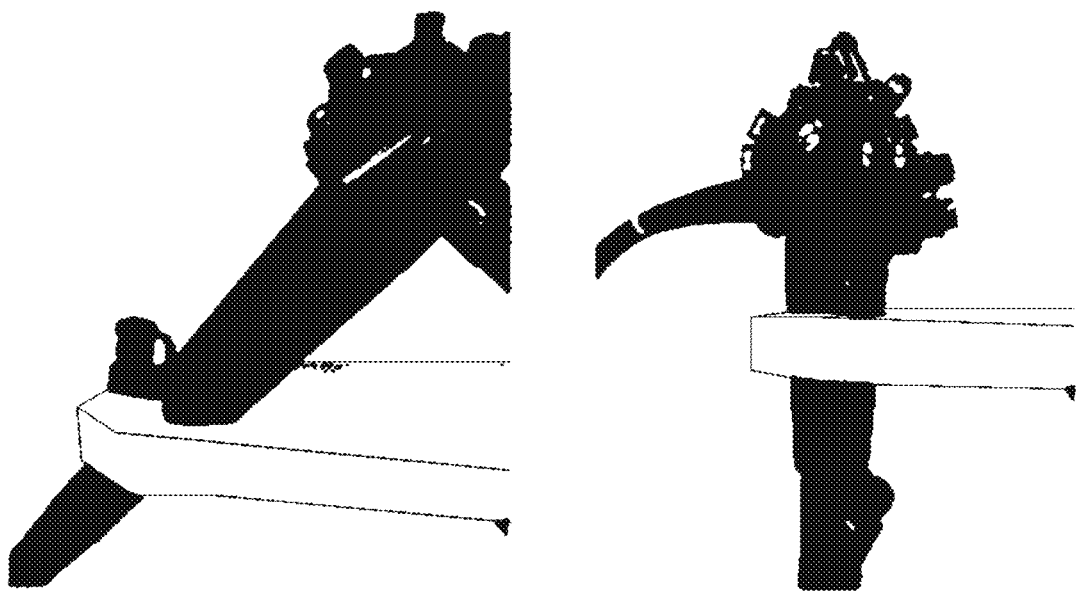
FIG. 6 is an image showing a state in which the endoscope operation part of the Pentax colonoscope is held at an oblique angle (left) or vertically (right) at one end of the scope hanger apical end part.

FIG. 6 shows a state that the endoscope operation part 2 of the Pentax colonoscope 1 is held at an oblique angle (left) or vertically (right) on one side (49 mm×31 mm in the bottom view) of the scope hanger apical end part 5.

Figure 7:
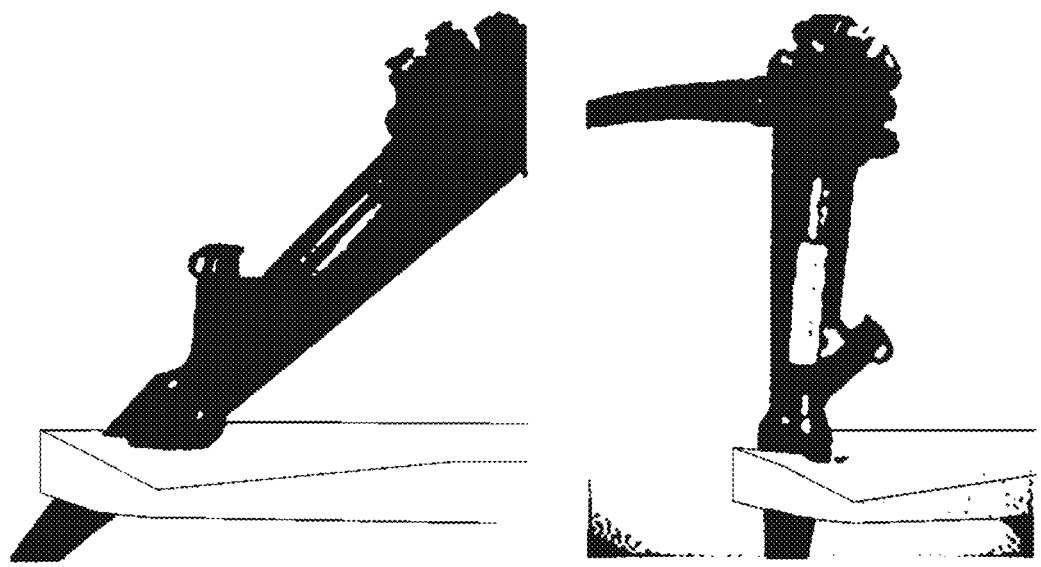
FIG. 7 is an image showing a state in which the endoscope operation part of the Olympus colonoscope is held at an oblique angle (left) or vertically (right) at the other end of the scope hanger apical end part.

In addition, FIG. 7 shows a state that the endoscope operation part 2 of the Olympus colonoscope 1 is held at an oblique angle (left) or vertically (right) on another side (45 mm×32 mm in the bottom view) of the scope hanger apical end part 5.

In the case that the endoscope operation part 2 is held by the scope hanger 3 at an oblique angle while the colonoscope 1 is inserted in the patient, the height of the scope hanger apical end part 5 needs to be lowered to the height held by the doctor (the height of 125 cm to 130 cm from the floor), that is, to the height of the upper end of the scope hanger outer cylinder part 7, so that the scope hanger inner cylinder part 6 was made possible to be raised and lowered.

When the endoscope operation part 2 is held vertically during standby (when the endoscope is not inserted in the patient), the height of the scope hanger apical end part 5 needs to be increased and the scope hanger inner cylinder part 6 needs to be fixed so that the apical end part of the endoscope does not contact with the floor, so that the scope hanger inner cylinder part 6 was made possible to be fixed to the scope hanger outer cylinder part 7 by screws 8.

When the endoscope operation part 2 is held at an oblique angle by the scope hanger 3 while the colonoscope 1 is inserted in the patient, the operation becomes simple (only lowering the scope hanger apical end part 5 as possible is sufficient) when the height of upper end part of the scope hanger outer cylinder part 7 is set as the lowered height of the scope hanger apical end part 5 becomes the height that a doctor holds (it is changed by doctor's physique), so that the scope hanger outer cylinder part 7 was made possible to be raised and lowered.

When the endoscope operation part 2 is held by the scope hanger 3 at an oblique angle while the colonoscope 1 is inserted in the patient, it was possible to hold the endoscope operation part 2 by simply rotating the scope hanger apical end part 5 with the height held by the doctor, that is, the height of the upper end of the scope hanger outer cylinder part 7, even without changing the height of the scope hanger apical end part 5 every time the depth of insertion of the colonoscope 1 or the position of the patient changes, so that the scope hanger apical end part 5 was made possible to be rotated.

Figure 8:
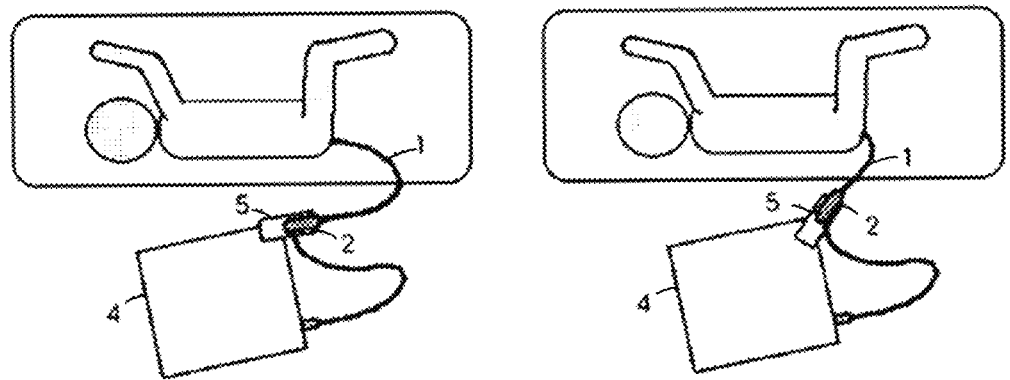
FIG. 8 is a plan view showing a state that the scope hanger apical end part is rotated vertically (left) when the insertion of the endoscope is shallow, and that the scope hanger apical end part is rotated so as to be oblique (right) when the insertion of the endoscope is deep, when the endoscope operation part of the colonoscope is held at an oblique angle.

FIG. 8 shows a state that the endoscope operation part 2 is held at the height of the upper end of the scope hanger outer cylinder part 7, when the colonoscope 1 is shallowly inserted, the scope hanger apical end part 5 is rotated so as to be vertical (left), and when the colonoscope 1 is deeply inserted, the scope hanger apical end part 5 is rotated so as to be oblique (right).

Figure 9:
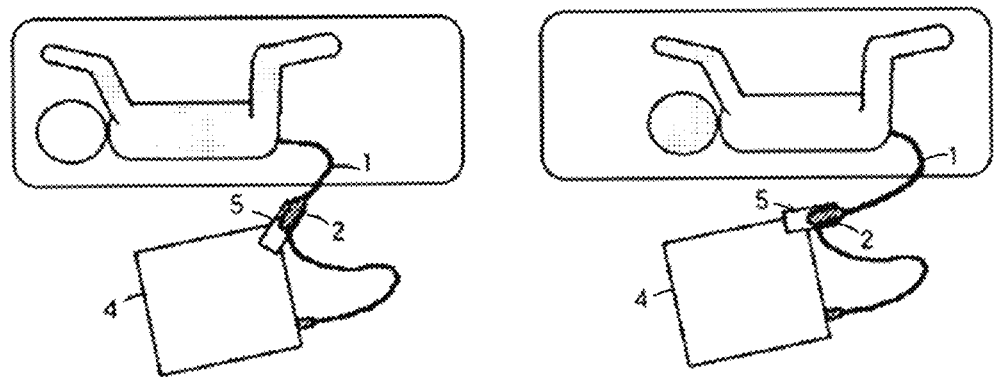
FIG. 9 is a plan view showing a state in which the scope hanger apical end part is rotated so as to be oblique (left) in case that the position of the patient is displaced to the head side, and the scope hanger apical end part is rotated so as to be vertical (right) in case that the position of the patient is displaced to the foot side when holding the endoscope operation part of the colonoscope at an oblique angle.

When using a colonoscope, the position of the patient is often changed by position change. FIG. 9 shows a state in which the scope hanger apical end part 5 is rotated so as to be oblique (left), in case that the position of the patient is displaced to the head side, and the scope hanger apical end part 5 is rotated so as to be vertical (right), in case that the position of the patient is displaced to the foot side, and the endoscope operation part 2 is held at the height of the upper end of the scope hanger outer cylinder part 7.

In addition, even when the position of the patient is displaced to the front side or the back side, the scope hanger apical end part 5 is rotated so that the endoscope operation part 2 can be held at the height of the upper end of the scope hanger outer cylinder part 7.

When the cart 4 was used actually on which the scope hanger 3 manufactured as described above is mounted, as shown in FIG. 1, while the colonoscope 1 is inserted in the patient, the endoscope operating part 2 could be held by the scope hanger 3 at an oblique angle with the same height as the doctor holds it.

Figure 10:
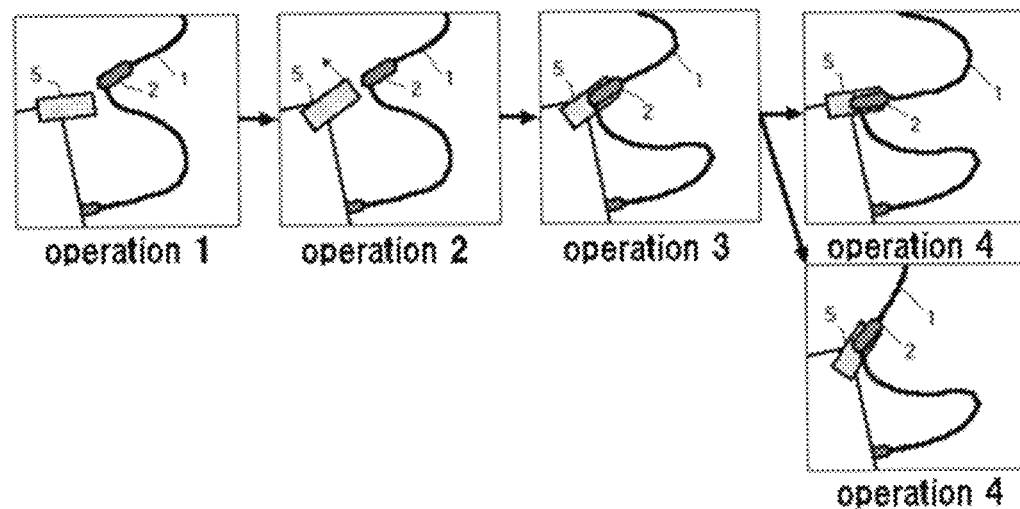
FIG. 10 is a plan view showing a method to hold the endoscope operation part of the colonoscope at an oblique angle.
Figure 11:
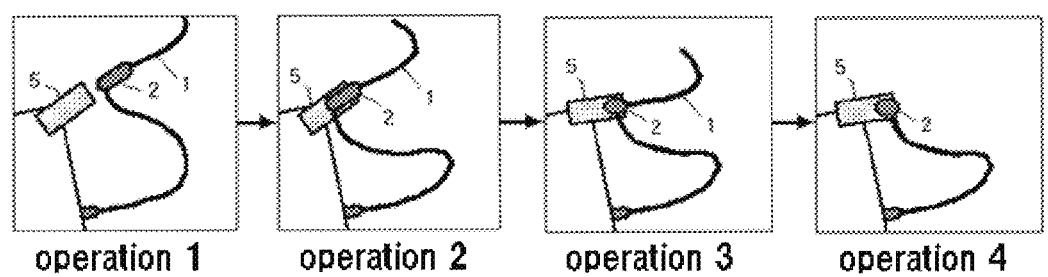
FIG. 11 is a plan view showing a method to hold the endoscope operation part vertically after use of the endoscope.

In FIGS. 10 and 11, the operation method of the scope hanger is shown in a plan view.

Now, at first, the operation to hold the endoscope operation part with the scope hanger is explained.
(1) The colonoscope 1 held with the right hand of the doctor is released (the colonoscope 1 is inserted in the patient so that the right hand can be released). Then the lower end of the endoscope operation part 2 is held with the right hand. Then the left hand becomes free (FIG. 10, operation 1).
(2) The screw 8 is loosen with the left hand, the scope hanger apical end part 5 is lowered to the height of the upper end of the scope hanger outer cylinder part 7 with the left hand, and simultaneously the scope hanger apical end part 5 is rotated to the patient side with the left hand (FIG. 10, operation 2).
(3) The endoscope operation part 2 held by the right hand is held with the left hand, and the endoscope operation part 2 is held with the scope hanger apical end part 5 at an oblique angle (FIG. 10, operation 3).
(4) In that case, the scope hanger apical end part 5 is rotated by the holding operation, when the insertion is shallow, the scope hanger apical end part 5 is rotated so as to be vertical, and when the insertion is deep, the scope hanger apical end part 5 is rotated so as to be oblique, and it is determined to be just right position. Therefore, the screw 8 shall not be tightened (FIG. 10, operation 4).

In the above operation method, there is no need to release the colonoscope 1 which is held by the doctor and of the assistant to hold, and there is no need to operate with both hands of the doctor.

In addition, when a doctor holds the endoscope operation part 2 held by the scope hanger once again, the endoscope operation part 2 can be detached with the left hand of the doctor with ease.

Next, the operation to hold the endoscope operation part by scope hanger after use of the endoscope is explained.
(1) After using the endoscope, the scope hanger apical end part 5 is lowered to the height of the upper end of the scope hanger outer cylinder part 7 (FIG. 11, operation 1).
(2) The endoscope operation part 2 held with the left hand is held at the scope hanger apical end part 5 at an oblique angle (FIG. 11, operation 2).
(3) While the endoscope operation part 2 is held by the scope hanger apical end part 5, the scope hanger apical end part 5 is rotated vertically using the lower end of the endoscope operation part 2, and simultaneously, the endoscope operation part 2 is rotated in a counterclockwise direction as seen from above, and the endoscope operation part 2 is held vertically at the scope hanger apical end part 5 (FIG. 11, operation 3).
(4) The scope hanger apical end part 5 is raised and supported with the left hand, the colonoscope 1 held with the right hand is hung down, the scope hanger apical end part 5 is supported with the right hand which was supported with the left hand, the screw 8 is tightened with the left hand (FIG. 11, operation 4).

The scope hanger of the present invention can be used for the conventional method of vertically holding the endoscope operation part of the gastroscope.

Also, in a facility where multiple doctors are enrolled, if a doctor does not wish to hold the endoscope operation part of the colonoscope at an oblique angle, the conventional usage method can be selected in which the endoscope operation part of the colonoscope is held vertically.

About Applied Products

By applying the cart having the scope hanger of the present invention, various endoscopes (a gastroscope, an enteroscope, a cholangiopancreatoscope, a laryngoscope, a bronchoscope, a cystoscope, an ureteroscope, a hysteroscope, an arthroscope, a neuroendoscope) can be held with the endoscope operation part while inserting in a patient.

At that time, in order to hold the various endoscopes at the same angle as the doctor holds, the range at which the oblique angle of the scope hanger apical end part can take is 20 to 80 degrees.

Actually, in the case of the bronchoscope, the oblique angle of the scope hanger apical end part takes an angle of 30 degrees, because the bronchoscope comes out upward from the mouth in the supine position, and in the case of the ureteroscope, the oblique angle of the scope hanger apical end part takes an angle of 70 degrees, because the ureteroscope comes out downward from the external urethral meatus in the crushing position.

The scope hanger of the present invention can be applied to a washing sink of an endoscope.

Figure 12:
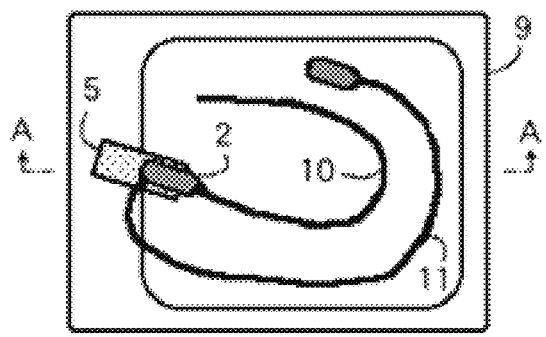
FIG. 12 is a plan view and section view showing a state holding the endoscope operation part on a scope hanger attached to washing sink at an oblique angle at the same height as the endoscopy technician holds.
Figure 12:
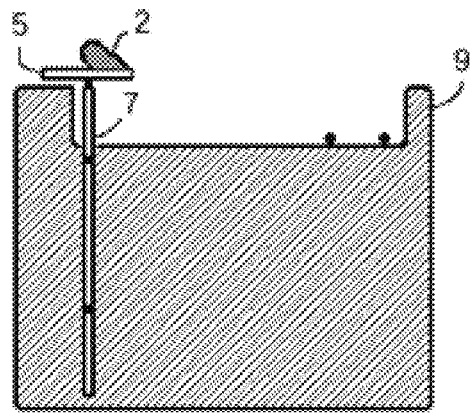

FIG. 12 shows a plan view and sectional view of a state in which the scope hanger attached to the washing sink 9 holds the endoscope operation part 2 at an oblique angle with the same height as the endoscopy technician holds.

When the endoscope 10 is placed on the bottom surface of the washing sink 9 and the endoscope operation part 2 is held by the scope hanger apical end part 5 at an oblique angle, in order to hold the endoscope operation part 2 at the position closest to the position the endoscopy technician holds, a scope hanger was installed on the left edge of the washing sink 9.

In order to place the endoscope 10 on the bottom surface of the washing sink 9 and to hold the endoscope operation part 2 at the scope hanger apical end part 5, it is thought that less unreasonable force is applied to the endoscope in the case that the endoscope operating part 2 is held at the same height and the same angle (that is, at an oblique angle) as the endoscopy technician holds.

Therefore, the height of the upper end of the scope hanger outer cylinder part 7 was adjusted at the height between 15 cm and 18 cm from the bottom surface of the washing sink 9 so that the height of the scope hanger apical end part 5 becomes the same height as the endoscopy technician holds.

Further, the scope hanger apical end part 5 was made possible to be rotated as the endoscope operation part 2 could be held regardless of the length of the endoscope 10 only by rotating the scope hanger apical end part 5 at the height of the upper end of the scope hanger outer cylinder part 7.

Figure 13:
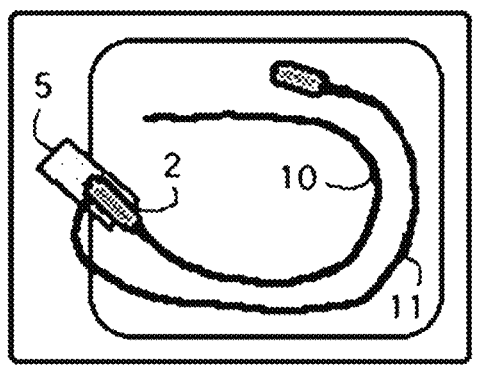
FIG. 13 is a plan view showing a state in which the scope hanger apical end part rotates obliquely (left) when the endoscope is long, and the scope hanger rotates so that the scope hanger apical end part turns sideways (right) when the endoscope is short when holding the endoscope operation part at an oblique angle by scope hanger attached to washing sink.
Figure 13:
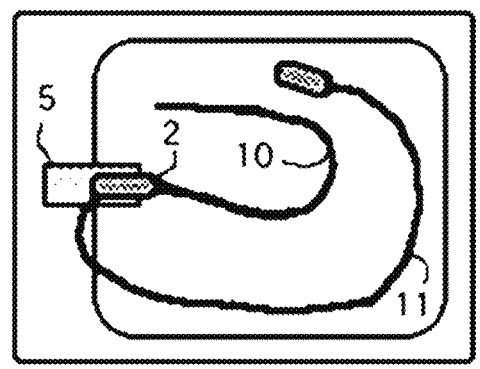

FIG. 13 shows a state that the endoscope operation part 2 is held by the scope hanger apical end part 5, by rotating the scope hanger apical end part 5 so as to be oblique (left) when the endoscope 10 is long, and by rotating to lie down (right) the scope hanger apical end part 5 when the endoscope 10 is short.

The washing sink 9 manufactured as described above was actually used. As shown in FIG. 12, when the endoscope 10 was placed on the bottom surface of the washing sink 9, the endoscope operation part 2 could be held by the scope hanger apical end part 5 at an oblique angle at the same height as the endoscopy technician holds.

Figure 14:
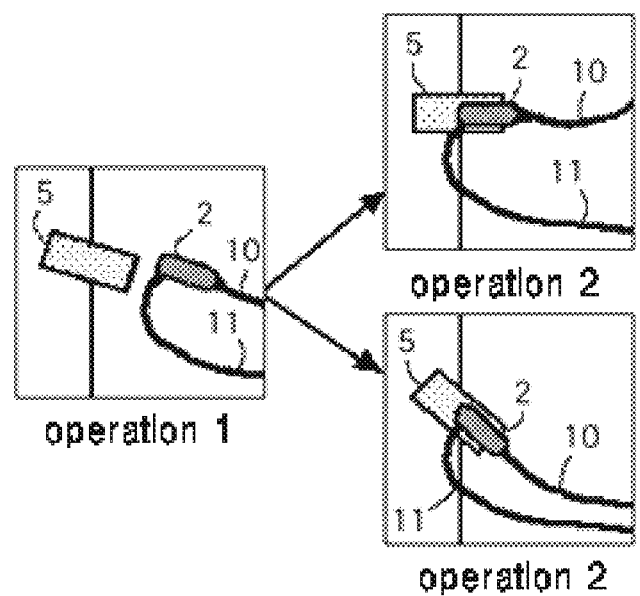
FIG. 14 is a plan view showing a method to hold the endoscope operation part at an oblique angle by scope hanger attached to washing sink.

FIG. 14 is a plan view showing a method of operating the scope hanger attached to the washing sink 9.

Now, the operation of holding the endoscope operation part on the scope hanger attached to the washing sink is explained.

(1) The endoscope 10 and the universal code part 11 is placed on the bottom surface of the washing sink 9 and the endoscope operation part 2 is held with the left hand of the endoscopy technician (FIG. 14, operation 1).

(2) The endoscope operation part 2 held by the left hand of the endoscopy technician is held by the scope hanger apical end part 5 at an oblique angle. In this case, the scope hanger apical end part 5 is rotated by the holding operation, when the endoscope 10 is short, the scope hanger apical end part 5 is rotated so as to lie down, and when the endoscope 10 is long, the scope hanger apical end part 5 is rotated so as to be oblique, to be determined to a right position (FIG. 14, operation 2).

Further, when the endoscope operation part 2 held by the scope hanger apical end part 5 is held again by the endoscopy technician, the endoscope operation part 2 is easily removed and held with the left hand of the endoscopy technician.

By holding the endoscope operation part 2 by the scope hanger attached to the washing sink 9, the hand of the endoscopy technician becomes free and washing of the endoscope surface and brushing of the endoscope channel becomes easy.

In addition, when the endoscope operation part 2 is held at an oblique angle by the scope hanger attached to the washing sink 9, since each entrance part of the endoscope channels faces upward, the brushing of the endoscope channel is easy to perform.

Since the scope hanger apical end part 5 of the present invention can hold endoscope operation parts 2 of various endoscopes of various manufacturers, various endoscopes of respective manufacturers can be washed with the same sink.

In addition, if the scope hanger of the present invention is attached to the washing and sterilizing apparatus, the endoscope operation part can be fixed in the sterilizing tank, so that the hand of the endoscopy technician becomes free, and attaching and detaching the tube to the endoscope channels can be performed with ease.

In addition, if the scope hanger of the present invention is attached to the stand, various endoscope of each manufacturer can be held at one place, so that a place where the sterilized endoscope is placed can be determined. If the endoscope is placed in that place, it can be recognized that it has been sterilized, so there is convenience that can prevent a medical accident that erroneously uses an unsterilized endoscope.

The scope hanger of the present invention is applicable to an endoscope storage cabinet.

Figure 15:
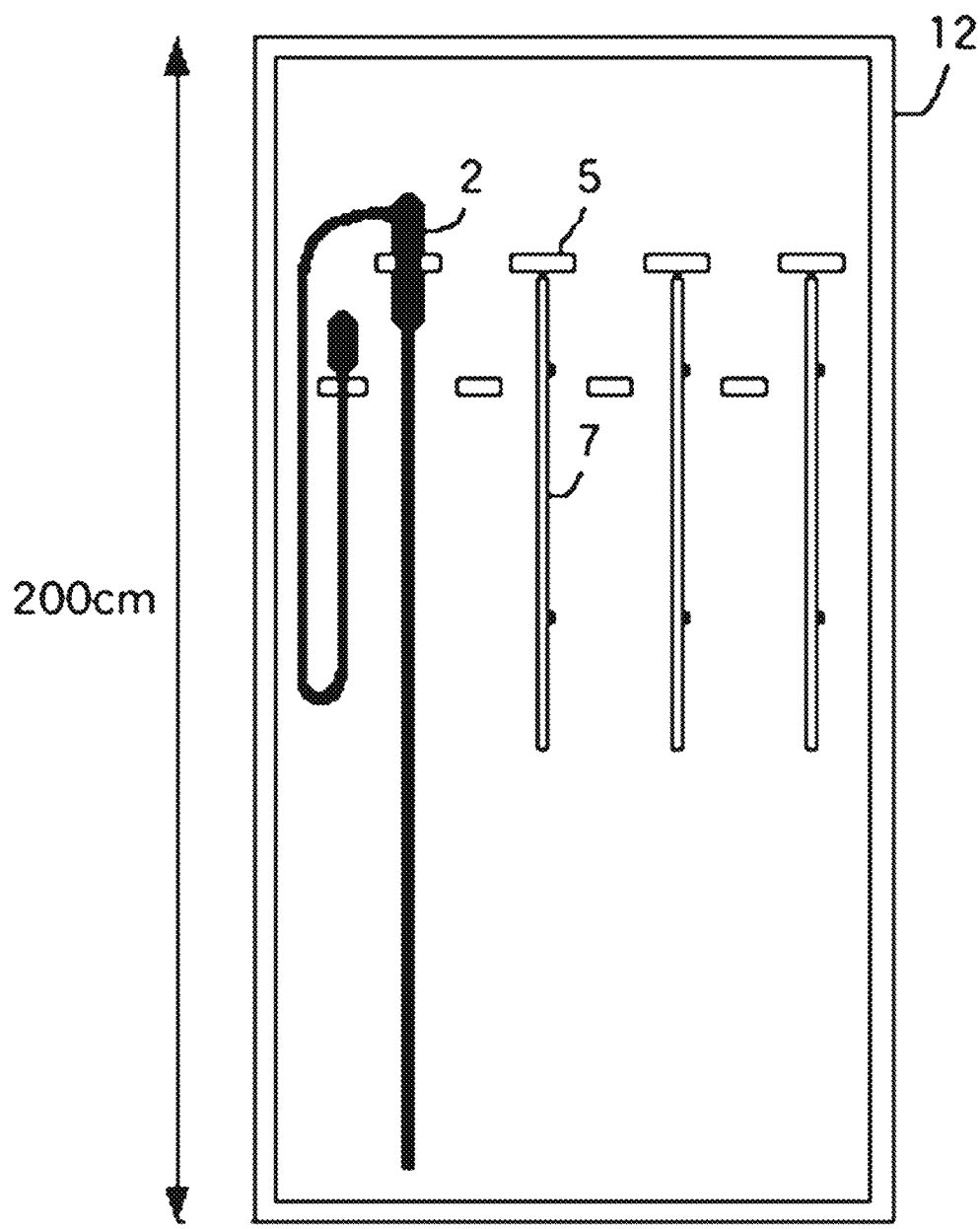
FIG. 15 is a front view showing a state holding the endoscope operation part vertically by scope hanger attached to endoscope storage cabinet.

FIG. 15 is a front view showing how the scope hanger attached to the endoscope storage cabinet 12 holds the endoscope operation part 2 vertically.

First, as shown in FIG. 15, a scope hanger was attached to the endoscope storage cabinet 12 arranging horizontally. In addition, the scope hanger apical end part 5 was made possible to be rotated to hold the endoscope operation part 2 of various endoscopes of various manufacturers.

When actually using the endoscope storage cabinet 12 manufactured as described above, it was possible to store various endoscopes of each manufacturer in the same place.

Therefore, in the endoscope storage cabinet 12 to which the scope hanger of the present invention is applied, it is possible to store endoscopes side by side in order of sterilization. By arranging the endoscopes in the order in which sterilization has been completed, it can be recognized that the endoscope has been sterilized, so that it is possible to prevent a medical accident inadvertently using an unsterilized endoscope.

As described above, by applying the scope hanger of the present invention to equipment such as washing sink, washing and sterilizing apparatus, stand, endoscope storage cabinet etc., while observing various endoscope washing and disinfection guidelines more reliably, it is possible to perform endoscope washing and sterilization.

INDUSTRIAL APPLICABILITY

The present invention can be applicable to manufacturer of medical devices or examination services.

DESCRIPTION OF THE REFERENCE NUMERALS

1. Colonoscope
2. Endoscope operation part
3. Scope hanger
4. Cart
5. Scope hanger apical end part
6. Scope hanger inner cylinder part
7. Scope hanger outer cylinder part
8. Screw
9. Washing sink
10. Endoscope
11. Universal code part
12. Endoscope storage cabinet

The invention claimed is:

1. An endoscope holding member, comprising:
a body comprising opposed major surfaces, a perimeter of a portion of the body defining a polygonal shape as viewed in a plan view of one of the opposed major surfaces; and
a recess formed in the body as viewed in the plan view, the recess having a shape wherein a portion of the recess has an elliptical curvature as viewed in the plan view and another portion of the recess has a circular curvature as viewed in the plan view, the recess defining a hole through the body as viewed in the plan view configured to hold an endoscope operation portion of an endoscope in the hole at an oblique angle with respect to one of the opposed major surfaces by a face and two contact points, the face contacting a lower surface of the endoscope operation portion and both a first point and a second point of the two contact points contacting an upper surface of the endoscope operation portion, the recess also defining an opening at the perimeter of the body in fluid communication with the hole that allows a forceps channel of the endoscope operation portion to be unobstructed with the endoscope operation portion held at the oblique angle.

2. The endoscope holding member according to claim 1, wherein the shape is further configured to hold the endoscope operation portion vertically.

3. The endoscope holding member according to claim 2, wherein:
the shape defines a proximal portion of the hole and a distal portion of the hole, and is configured such that a hardness adjusting ring of the endoscope operation portion can be passed vertically through the proximal portion of the hole and the endoscope operation portion can be horizontally moved into the distal portion of the hole and held vertically by the distal portion of the hole.

4. The endoscope holding member according to claim 1, wherein the endoscope holding member has a thickness of 1 cm to 5 cm, a length of 8 cm to 15 cm, and a width of 20 cm to 30 cm.

5. The endoscope holding member according to claim 1 wherein said oblique angle is 20 to 80 degrees.

6. The endoscope holding member according to claim 1, further comprising a plurality of holes, the plurality of holes being in the range of 2 to 24 holes, the plurality of holes including the hole through the body as viewed in the plan view.

7. The endoscope holding member according to claim 1, wherein the endoscope holding member is configured to respond to changes in an insertion length of the endoscope and a position of a patient by rotating the endoscope holding member with respect to a support portion at a height of an upper end of a support portion which is set to the height held by a doctor in advance.

8. The endoscope holding member according to claim 1, wherein the endoscope holding member is configured to hold multiple different shapes of endoscopes.

9. The endoscope holding member according to claim 8, which is supported by a support portion so as to be rotatable in a horizontal direction with respect to a mount that is mountable to a stand or an endoscope storage cabinet.

10. The endoscope holding member according to claim 9, wherein the endoscope holding member is configured to hold the endoscope vertically.

11. The endoscope holding member according to claim 8, which is supported by a support portion so as to be rotatable in a horizontal direction with respect to a mount that is mountable to a washing sink or a washing and sterilizing apparatus.

12. The endoscope holding member according to claim 11, wherein the endoscope holding member is configured to hold the endoscope being washed or sterilized at an oblique angle for liberating the hands of an endoscopy technician and stably performing a washing or sterilizing procedure.

13. The endoscope holding member according to claim 1, wherein:
the endoscope holding member is supported by a support portion so as to be rotatable in a horizontal direction and vertically movable with respect to a mount that is mountable to a cart;
the endoscope holding member is configured to hold the endoscope inserted in a patient at the oblique angle for liberating hands of an operator, preventing radiation exposure by leaving the X-ray room, performing emergency procedures, adjusting endoscopic devices by using an operator's hands, or resting a tired operator's hands; and
the endoscope holding member is configured to hold the endoscope not inserted in the patient vertically before use or after use.

14. The endoscope holding member according to claim 13, comprising two or more support portions.

15. The endoscope holding member according to claim 13, comprising said support portion at a right end of a front face of the cart.

16. The endoscope holding member according to claim 1, wherein:
the shape defines a proximal portion of the hole and a distal portion of the hole, and is configured such that a hardness adjusting ring of the endoscope operation portion can be passed vertically through the proximal portion of the hole and the endoscope operation portion can be horizontally moved into the distal portion of the hole and held by the distal portion of the hole at the oblique angle.

17. A washing sink, a washing and sterilizing apparatus, a stand or an endoscope storage cabinet, comprising the holding member described in claim 1.

18. A washing sink, a washing and sterilizing apparatus, a stand or an endoscope storage cabinet according to claim 17 wherein said holding member is rotatably supported.

19. A method for holding an endoscope stably using the endoscope holding member according to claim 1, comprising:
passing a hardness adjusting ring of the endoscope operation portion vertically through a proximal portion of the hole;

moving the endoscope operation portion horizontally into a distal portion of the hole; and holding the endoscope operation portion at the oblique angle in the distal portion of the hole.

20. A method according to claim 19, wherein the endoscope operation portion is supported at the oblique angle by the face and the two contact points.

* * * * *